(12) United States Patent
Krzyzanowski (10) Patent No.: US 8,394,120 B2
(45) Date of Patent: Mar. 12, 2013

(54) END EFFECTOR ASSEMBLY WITH INCREASED CLAMPING FORCE FOR A SURGICAL INSTRUMENT

(76) Inventor: Jacek Krzyzanowski, Etobicoke (CA)

(*) Notice: Subject to any disclaimer, the term of this patent is extended or adjusted under 35 U.S.C. 154(b) by 186 days.

(21) Appl. No.: 12/773,207

(22) Filed: May 4, 2010

(65) Prior Publication Data

US 2011/0276085 A1 Nov. 10, 2011

(51) Int. Cl.
*A61B 17/00* (2006.01)
(52) U.S. Cl. ..................... 606/208
(58) Field of Classification Search .......... 606/205–209, 606/51–52, 142–143
See application file for complete search history.

(56) References Cited

U.S. PATENT DOCUMENTS

| | | | |
|---|---|---|---|
| 4,763,668 A | 8/1988 | Macek | |
| 4,887,612 A | 12/1989 | Esser et al. | |
| 5,133,727 A | 7/1992 | Bales et al. | |
| 5,507,773 A * | 4/1996 | Huitema et al. | 606/207 |
| 5,582,617 A * | 12/1996 | Klieman et al. | 606/170 |
| 5,951,581 A * | 9/1999 | Saadat et al. | 606/170 |
| 6,273,860 B1 | 8/2001 | Kostylev et al. | |
| 6,309,404 B1 | 10/2001 | Krzyzanowski | |
| 7,105,000 B2 | 9/2006 | McBrayer | |
| 7,223,272 B2 | 5/2007 | Francese et al. | |
| 7,232,445 B2 | 6/2007 | Kortenbach et al. | |
| 7,566,300 B2 * | 7/2009 | Devierre et al. | 600/104 |
| 2005/0182426 A1 * | 8/2005 | Adams et al. | 606/142 |
| 2008/0207995 A1 | 8/2008 | Kortenbach et al. | |
| 2008/0262525 A1 * | 10/2008 | Chang et al. | 606/170 |
| 2008/0294178 A1 | 11/2008 | Kortenbach et al. | |

* cited by examiner

*Primary Examiner* — Gary Jackson
*Assistant Examiner* — Martin Ton
(74) *Attorney, Agent, or Firm* — Norton Rose Canada LLP (57) ABSTRACT

An end effector assembly with increased clamping force for a surgical instrument including a hollow shaft having a proximal end and a distal end, a clevis coupled to the distal end of the hollow shaft, a flat support coupled to the clevis, a deflection member, a procedural member assembly rotatably coupled to the flat support and a pair of actuation means attached to the procedural member assembly and slidable relative to the hollow shaft for rotationally moving the procedural member assembly between a closed and an open position wherein the deflection member engaged the actuation means. The deflection member may be integral with the clevis, coupled to the clevis and the flat support, coupled to just the flat support, may be adjustable or rotatable or coupled to hollow shaft.

21 Claims, 11 Drawing Sheets

Design Constraints (Constants):
$F_l$ is the loading force applied to the end effector.
$F_{C1}$ is clamping force with no deflection angle.
A is the horizontal offset between pivot and actuating holes.
B is the vertical offset between pivot and actuating holes.
θ is the angle between pivot and actuating holes, θ is dependent on A and B: $\sin(\theta) = A/(A^2+B^2)^{-2}$, $\cos(\theta) = B/(A^2+B^2)^{-2}$.

Definitions:
β is the deflection angle.
$F_C$ is the clamping force with deflection angle β.

Derviation:
$F_C = F_l*\cos[(\pi/2)-\beta-\theta]$, let $\alpha = \theta+\beta$, then
$F_C = F_l*\cos[(\pi/2)-\alpha]$, using cosine subtraction theorems, then
$F_C = F_l*[\cos(\pi/2)\cos(\alpha)+\sin(\pi/2)\sin(\alpha)]$,
$= F_l*\sin(\alpha)$,
$= F_l*\sin(\theta+\beta)$, using sine addition theorems, then
$F_C = F_l*[\sin(\theta)\cos(\beta)+\cos(\theta)\sin(\beta)]$, apply design constraints
$F_C = F_l*[A*\cos(\beta)/(A^2+B^2)^{-2}+B*\sin(\beta)/(A^2+B^2)^{-2}]$,
$F_C = F_l*[A*\cos(\beta)+B*\sin(\beta)]/(A^2+B^2)^{-2}$
where $0° \leq \beta \leq 90°-\theta$ (physical constraints)

Fig. 24

Design Constraints (Constants):
$F_l$ is the loading force applied to the end effector.
A is the horizontal offset between pivot and actuating holes.
B is the vertical offset between pivot and actuating holes.
C is the horizontal offset between deflection member and actuating hole.
D is the vertical offset between deflection member and actuating hole.
θ is the angle between pivot and actuating holes, θ is dependent on A and B: $\sin(\theta) = A/(A^2+B^2)^{-2}$, $\cos(\theta) = B/(A^2+B^2)^{-2}$.

Definitions:
β is the deflection angle.
$F_C$ is the clamping force with deflection angle β.

From Fig. 24,
$F_C = F_l * [A*\cos(\beta)+B*\sin(\beta)]/(A^2+B^2)^{-2}$
where $0° \leq \beta \leq 90°-\theta$ (physical constraints)

From Fig. 25,
β α C
As C increases and D stays the same, then β increases and therefore $F_C$ increases.

END EFFECTOR ASSEMBLY WITH INCREASED CLAMPING FORCE FOR A SURGICAL INSTRUMENT

FIELD OF THE INVENTION

This invention relates in general to an end effector with increased clamping force for a surgical instrument and more particularly to end effectors of biopsy forceps or end effectors of endoscopic instruments for use through or with an endoscope.

BACKGROUND OF THE INVENTION

Biopsy forceps are commonly used during endoscopic procedures for removing tissue samples for pathological examination or for therapeutic purposes. For effective sampling it is important that a maximum force be transmitted from the handle of the endoscopic instrument to the end effector. Large clamping forces are often difficult to achieve due to the size restrictions of the end effector. Typically the arm of the lever, the dimensions or distances between the jaws or procedural member's pivot axis and the actuating hole are relatively short, which therefore limits the mechanical leverage of the end effector. It is especially evident when the procedural members are in a closed or nearly closed position. The procedural members therefore have small clamping forces resulting in poor grasping and retention of the tissue sample.

An endoscopic end effector with increased clamping force may be achieved by the deflection of the actuation means over the deflection member in the vicinity of the actuating hole. Increased clamping force is most required when the end effector procedural members are in the closed or nearly closed position.

Deflection of the actuation means changes the distribution of the pulling force applied to the handle of the endoscopic tool by the operator and transmitted by the actuation means to the end effector mechanism. The distribution of the forces is such that the clamping force is higher versus a clamping force derived only from the lever arm between the pivot axis of the jaws and the actuating hole.

Typical endoscopic surgical tools comprise of the handle actuating the end effector and end effector with procedural members performing a function. A hollow shaft or member extends between the handle and the end effector. The hollow member houses the actuation means that convert the actuation of the handle into the actuation of the procedural members of the end effector. The end effector is attached to the distal end of the hollow member and the handle is attached to the proximal end of the conduit.

Typical endoscopic end effectors comprise of procedural members and a clevis encompassing the procedural members. Actuation means are rotatably connected to the arms of the procedural members through the actuating holes. Proximal ends of the actuation means are attached to the movable sliding element of the handle. Procedural members are connected together by a rivet passing through the pivot axis holes. Often a flat member is present between the procedural members. The flat member may have a hole that accepts the rivet and is axial or nearly axial with the pivot axis holes of the procedural members. In essence the procedural members and the flat member are sandwiched pivotally together by the encompassing rivet. Often the clevis is also incorporated into this sandwich.

Prior art end effectors have been devised to address the some of the noted problems. For example, U.S. Pat. No. 4,763,668 issued to Macek on Aug. 16, 1988 et al discloses a biopsy forceps jaw assembly utilizing a linkage mechanism for the actuation of the jaws. The linkage mechanism provides increased clamping force. However the assembly process of the jaws and the number of individual components makes the device expensive to manufacture.

U.S. Pat. No. 4,887,612 issued on Dec. 19, 1989 to Esser et al discloses a biopsy forceps jaws mechanism which utilizes a cam linkage to actuate the jaws. In the closed or nearly closed position of the jaws this design does not offer an increased clamping force. Furthermore, the components of the jaws require expensive machining process and are not ideally suited for mass production of the disposable biopsy forceps.

U.S. Pat. No. 5,133,727 issued on Jul. 28, 1992 to Bales et al teaches a simplified construction of the biopsy forceps jaws using two actuating wires for the actuation of the jaws. This construction is suitable for mass production and assembly of the disposable biopsy forceps. However the clamping force of the jaws is less than in the linkage design. This manifests itself specifically when the jaws are in the closed or almost closed position. As noted above the clamping force is determined by the lateral distance between the pivot axis of the jaws and the actuation holes and it is limited by the constraints of the size of the channel that the jaws have to pass through during a procedure.

Figure 5:
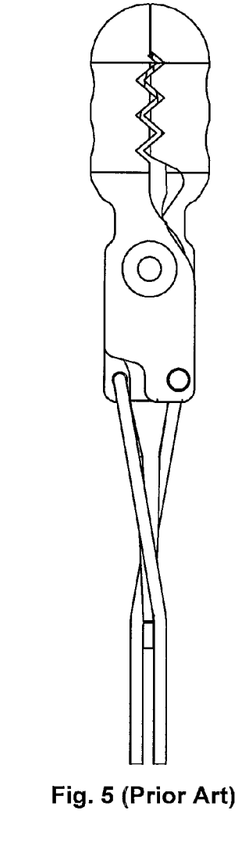
FIG. 5 in a side elevational view, illustrates the end effector assembly of the prior art.
Figure 6:
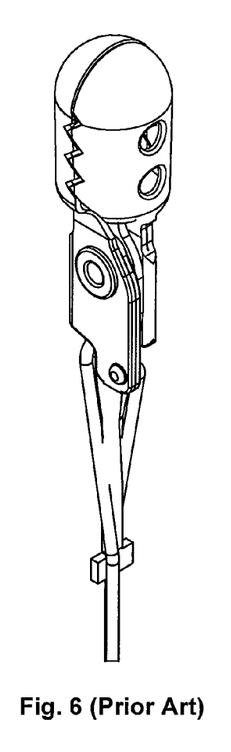
FIG. 6 in a perspective view, illustrates the end effector assembly of FIG. 5.
Figure 7:
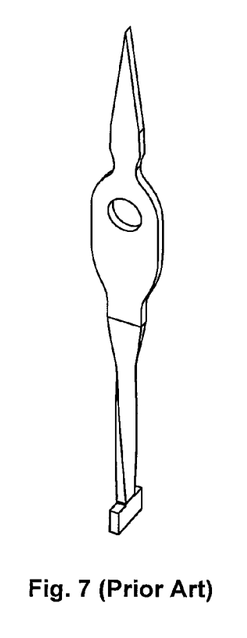
FIG. 7 in a perspective view, illustrates the twisted flat support of the end effector assembly of FIG. 5.

Referring to FIGS. 5 to 7, Boston Scientific Corporation Radial Jaw® 3 and Radial Jaw® 4 both incorporate a twist in a proximal end of the flat needle in the construction of the jaws. This twist provides for a limited deflection of the actuating wires and increased clamping force of the closing jaws. The twist is located at a distance from the actuating holes of the jaws therefore limiting the deflection angle and the resulting mechanical advantage. Also the twisted wings at the proximal end of flat needle flex back when tensioned by the actuating wires, therefore reducing the deflection angle and reducing the increase of the clamping force of the device. Furthermore, the stainless steel actuating wires rub against stainless steel twist which creates rough feel during the actuation of the jaws. Medical professionals prefer smooth opening and closing of the biopsy forceps.

U.S. Pat. No. 6,273,860 issued Aug. 14, 2001 to Kostylev et al discloses a design of the jaws assembly providing an increased clamping force of the biopsy forceps, especially as the jaws approach the closed position. The proposed design involves grooves around the back of the jaws and control wires sliding within these grooves. The construction of jaws proposed by Kostylev is expensive to manufacture and therefore not suitable for the mass production of the disposable biopsy forceps.

U.S. Pat. No. 7,105,000 issued Sep. 12, 2006 to McBrayer teaches us that the higher clamping force can be obtained by incorporating a circumferential ridge on the clevis. This ridge allows for an increased spacing between the pivot axis of the jaws and the actuating holes and therefore an increased clamping force of the closing jaws. The ridge however increases the diameter of the clevis. The diameter of the clevis is limited by the diameter of the channel in the endoscope through which the devices has to be pushed. Consequently, the increased clamping force is also limited by the diameter of the channel of the endoscope.

U.S. Pat. No. 7,223,272 issued May 29, 2007 to Francese et al proposes mounting of the jaws on non-collinear axes. This allows for increased spacing between the pivot axis of the jaws and the actuating holes, without an increase of the diameter of the clevis, and consequently an increased clamping forceps of the closing jaws. This design is however more complicated versus a design having just one pivot axis and therefore more expensive to manufacture.

Thus an end effector for a surgical instrument which has improved clamping force, easily fits within the diameter of the channel of the endoscope, is suited for mass production, is economical to machine process, allows for smooth operation, is disposable, and has an efficient and effective design is desirable.

SUMMARY OF THE INVENTION

An object of one aspect of the present invention is to provide an improved end effector for surgical instrument with improved clamping force.

In accordance with one aspect of the present invention there is provided an end effector assembly with increased clamping force for a surgical instrument including a hollow shaft having a proximal end and a distal end, a clevis coupled to the distal end of the hollow shaft, an optional flat support coupled to the clevis, a deflection member integral with the clevis, a procedural member assembly rotatably coupled to the flat support or to the clevis or to both and a pair of actuation means attached to the procedural member assembly and slidable relative to the hollow shaft for rotationally moving the procedural member assembly between a closed and an open position when the deflection member engages the actuation means.

The engagement of the actuation means by the deflection member can result in an increased clamping force when the procedural member assembly is in the closed position. Furthermore, the clamping force will reach a maximum value for a specific deflection angle for the given design constrains.

In accordance with another aspect of the present invention there is provided an end effector assembly with increased clamping force for a surgical instrument where the deflection member may be coupled to the clevis and the flat support.

In accordance with another embodiment of the present invention, the deflection member may be coupled to just the flat support.

In accordance with another aspect of the present invention the deflection member may be coupled to hollow shaft or be integral with the hollow shaft.

Conveniently, the deflection member may be rotatable or have an adjustable position and may comprise of lubricious material.

An advantage of the present invention is the increased clamping force at the end effector when the procedural members are in the closed or nearly closed or clamping position due the inclusion of the deflection member.

BRIEF DESCRIPTION OF THE DRAWINGS

A detailed description of the preferred embodiments is provided herein below by way of example only and with reference to the following drawings, in which.

In the drawings, preferred embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

Figure 1:
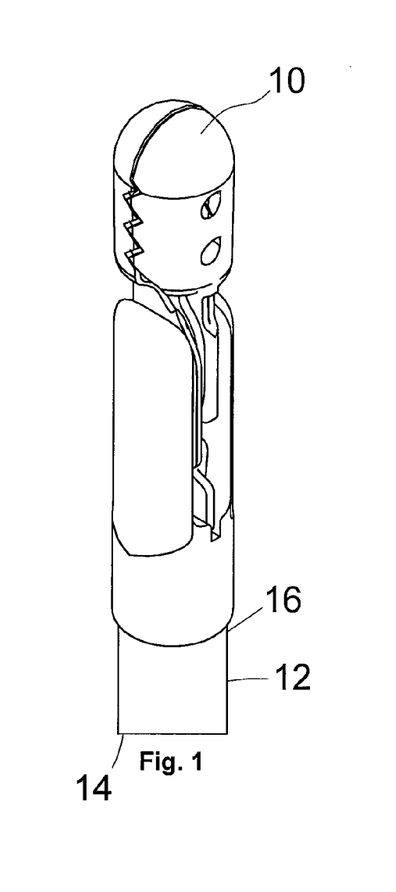
FIG. 1 in a perspective view, illustrates an end effector assembly with increased clamping force for a surgical instrument in accordance with a preferred embodiment of the present invention.
Figure 2:
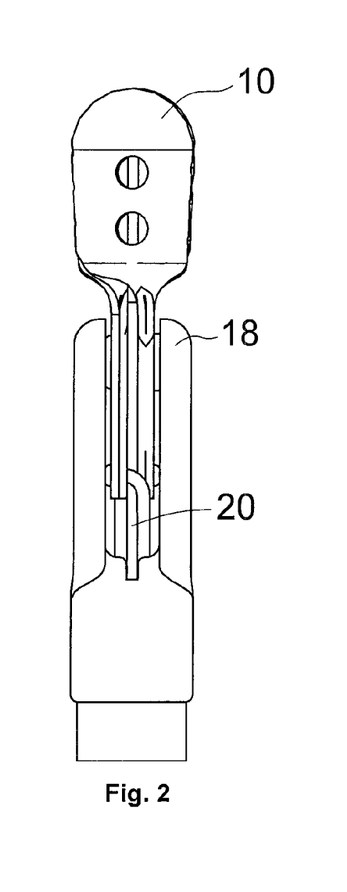
FIG. 2 in a top plan view, illustrates the end effector assembly of FIG. 1.
Figure 3:
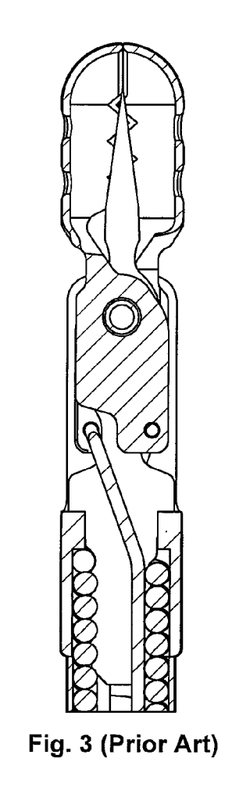
FIG. 3 in a partial sectional view, illustrates an end effector assembly of the prior art. The end effector is in a closed position with pulling force not applied.
Figure 4:
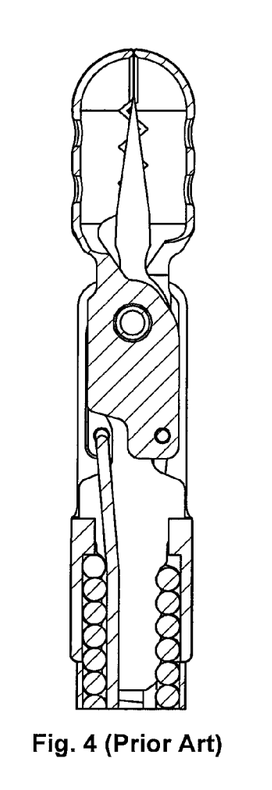
FIG. 4 in a partial sectional view, illustrates the end effector assembly of FIG. 3. in a closed position and with pulling force applied and consequently straightened actuation means.

Referring to FIGS. 1 and 2, there is illustrated in perspective and top plan views, an end effector assembly with increased clamping force in accordance with a preferred embodiment of the present invention. The end effector assembly 10 with increased clamping force for a surgical instrument includes a hollow shaft 12 having a proximal end 14 and a distal end 16. The end effector assembly 10 further includes a clevis 18 coupled to the distal end 16 of the hollow shaft 12 and an optimal flat support 20 which is coupled to the clevis 18.

Figure 8:
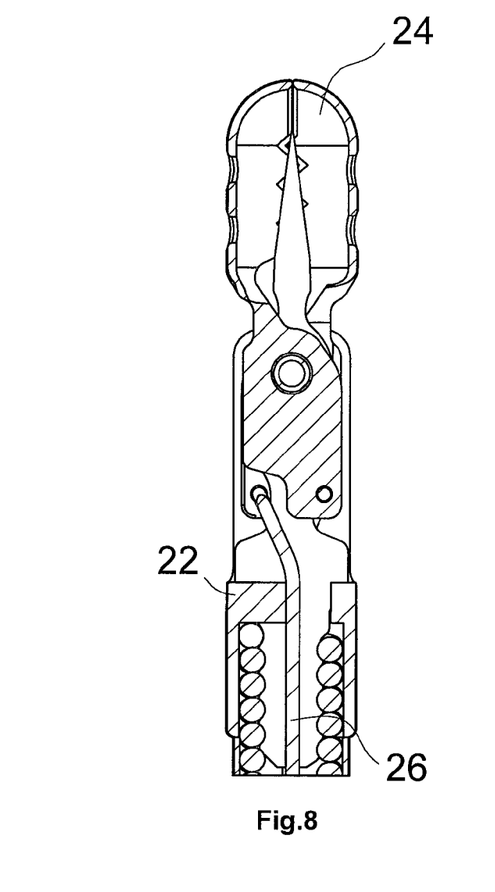
FIG. 8 in a partial sectional view, illustrates the end effector assembly of FIG. 1 where the defection member is coupled to the clevis.
Figure 9:
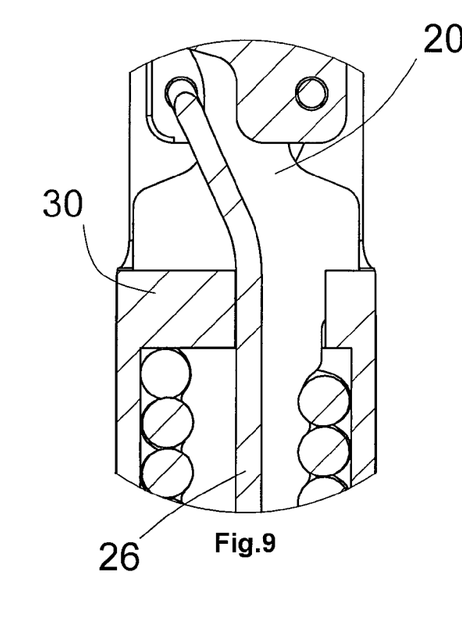
FIG. 9 in a partial sectional view, illustrates the end effector assembly of FIG. 8.

Referring to FIGS. 8 and 9, the end effector assembly 10 further includes in one embodiment, a deflection member 22 that is integral with the clevis 18. The end effector assembly 10 also includes a procedural member assembly 24 that is rotatably coupled to the flat support 20 and an actuation means 26 that are attached to the procedural member assembly 24. The actuation means 26 are slidable relative to the hollow shaft 12 and allow for the rotational movement of the procedural member assembly 24 between a closed and an open position when the actuation means 26 engage with the deflection member 22. The deflection member 22 may be further defined as an integral shoulder 30 of the clevis 18 that extends out from the clevis 18 so as to engage the actuation means 26 as they extend through the clevis 18 to the proximal end 14 of the hollow shaft. The engagement of the actuation means 26 with the integral shoulder 30 results in the increased clamping force of the end effector assembly 10 when the procedural member assembly 24 is in the closed or nearly closed position. The integral shoulder 30 may also include a lubricious material for reducing friction when the actuation means 26 slide against the integral shoulder 30 to allow for smooth operation.

Figure 10:
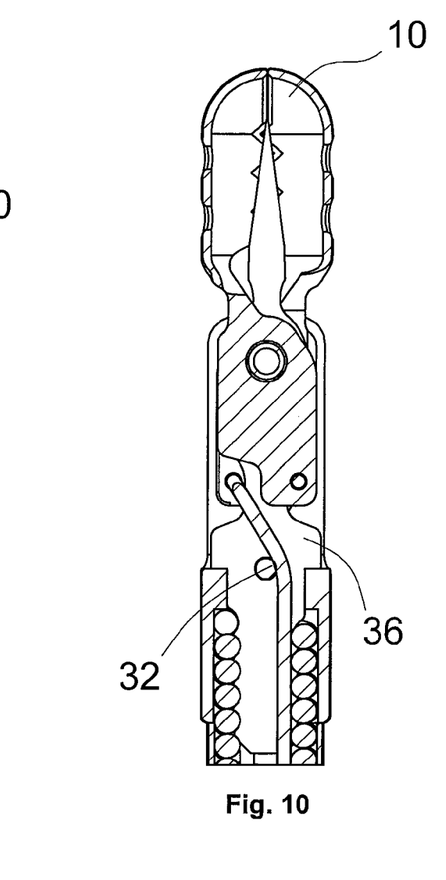
FIG. 10 in a partial sectional view, illustrates the end effector assembly of FIG. 1 where the deflection member is coupled to the clevis and the flat support.
Figure 11:
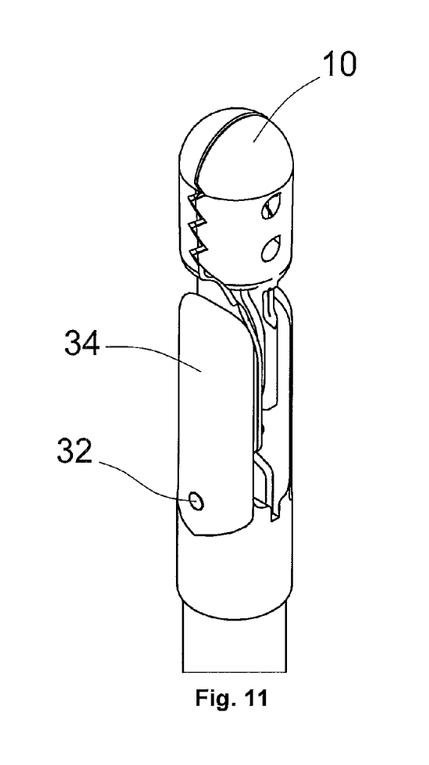
FIG. 11 in a perspective view, illustrates the end effector assembly of FIG. 10.
Figure 12:
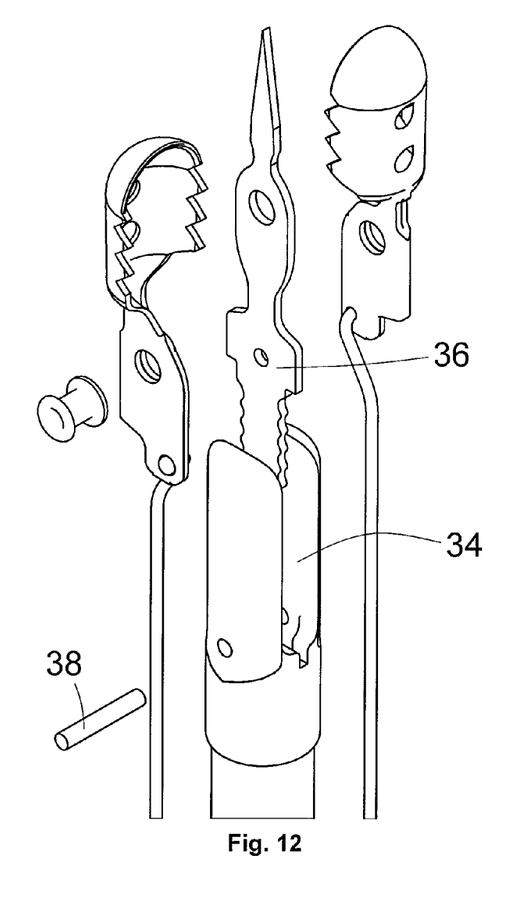
FIG. 12 in an exploded view, illustrates the end effector of FIG. 10.
Figure 13:
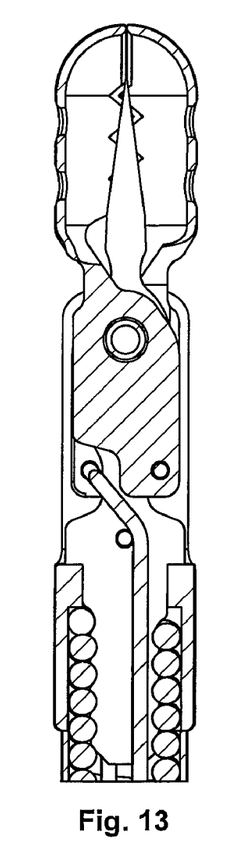
FIGS. 13, 14 and 15 in partial sectional views, illustrate the end effector assembly of FIG. 10 showing the changes in defection angle of the actuation means as the deflection member position is varied.
Figure 14:
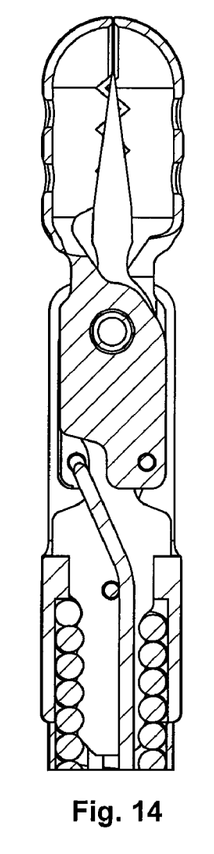
Figure 15:
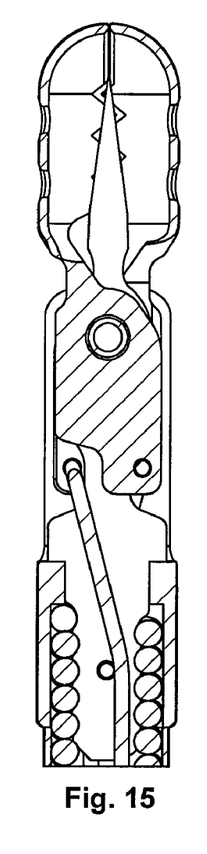

Referring to FIGS. 10 to 12 in a second embodiment of the present invention, the deflection member 32 may be coupled to the clevis 34 and a flat support 36. The deflection member 32 may be further defined as a pin 38 that passes through a series of apertures in the clevis 34 and the flat support 36. The engagement of the actuation means 26 against the pin 38 results in the increased clamping force of the end effector assembly 10 when the procedural member assembly 24 is in the closed or nearly closed position. The pin 38 may further include a lubricious material for reducing friction when the actuation means 26 slide against the pin 38 to allow for smooth operation. The pin 38 may also be rotatable within the apertures of the clevis 34 and the flat support 36 so as to also aid in the smooth operation of the end effector assembly 10.

Figure 16:
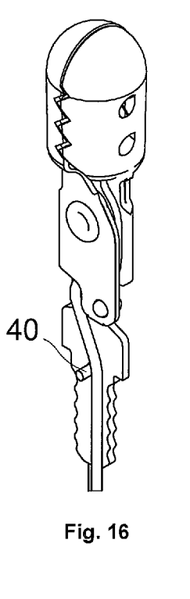
FIG. 16 in a perspective view, illustrates the end effector assembly of FIG. 1 where the deflection member is coupled to the flat member.
Figure 17:
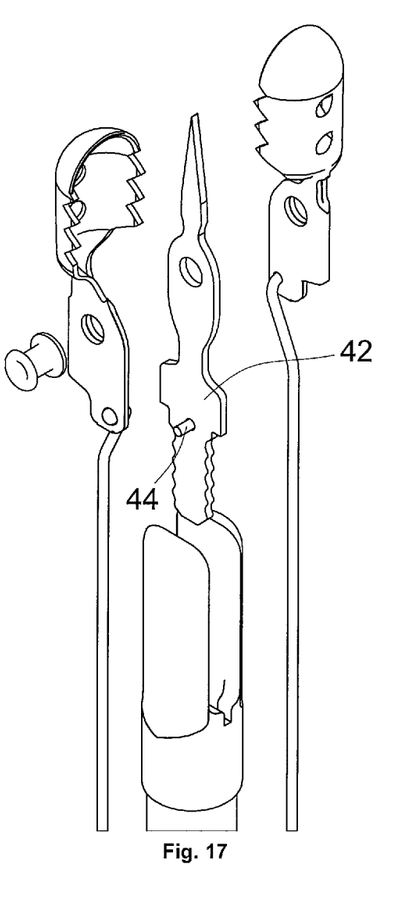
FIG. 17 in an exploded view illustrates the end effector assembly of FIG. 16.

Referring to FIGS. 16 and 17 in a third embodiment of the present invention, the deflection member 40 may be coupled to the flat support 42 only. The deflection member 40 may be further defined as a pin 44 that passes through an aperture in the flat support 42. The engagement of the actuation means 26 against the pin 44 results in the increased clamping force of the end effector assembly 10 when the procedural member assembly 24 is in the closed or nearly closed position. The pin 44 may further include a lubricious material for reducing friction when the actuation means 26 slide against the pin 44 to allow for smooth operation. The pin 44 may also be rotatable within the aperture of the flat support 42.

Figure 18:
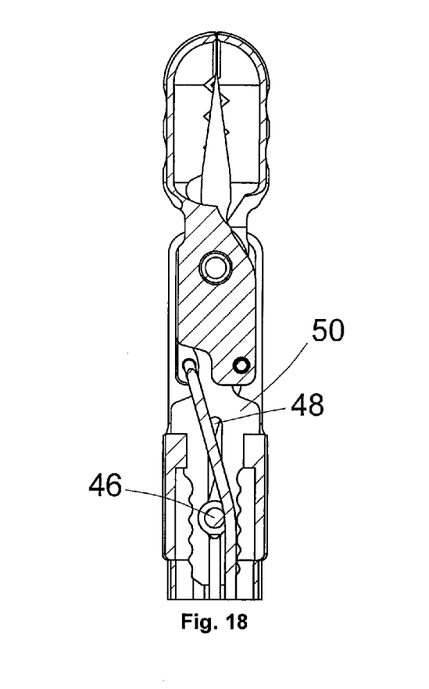
FIG. 18 in a partial sectional view, illustrates the end effector assembly of FIG. 1 where the position of the deflection member is adjustable along a slot in the flat member.
Figure 19:
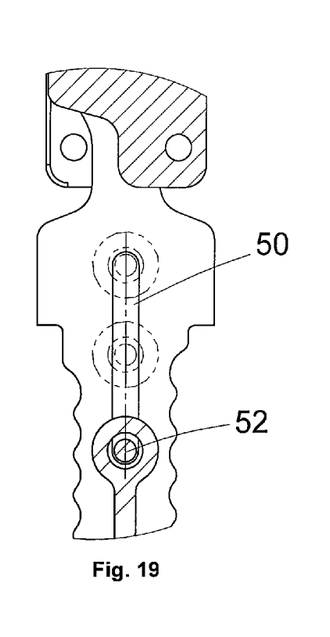
FIG. 19 in a partial sectional view, illustrates the positioning of the deflection member within the slot of the end effector assembly of FIG. 18.
Figure 20:
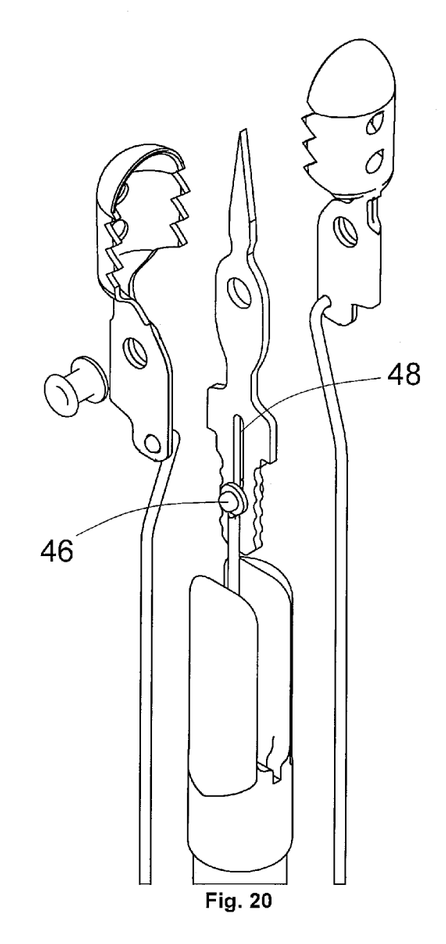
FIG. 20 in an exploded view, illustrates the end effector assembly of FIG. 18.

Referring to FIGS. 18 to 20 in a fourth embodiment of the present invention, the deflection member 46 may be moveably coupled within a slot 48 located in the flat support 50. The deflection member 46 may be further defined as a pin 52 that passes through the slot 48 in the flat support 50. The slot 48 allows for the dynamic movement of the pin 52 within the slot 48. The ability to vary the position of the deflection member 46 or pin 52, changes the angle of deflection of the actuation means 26 and therefore the clamping force can vary as well. Therefore, the slot 48 allows for the dynamic changes to the clamping force of the end effector assembly 10. The pin 52 may further include a lubricious material for reducing friction when the actuation means 26 slide against the pin 52 to allow for smooth operation. The pin 52 may also be rotatable within the slot 48 of the flat support 50.

Figure 21:
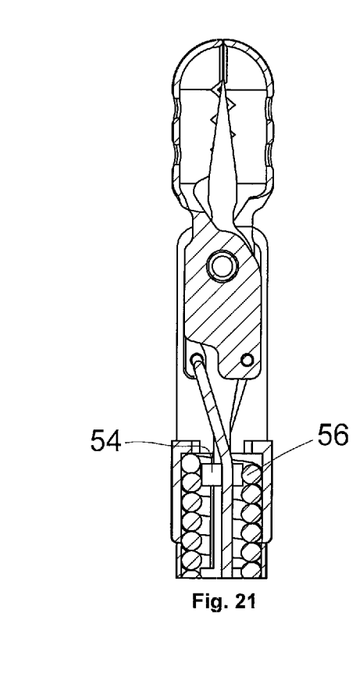
FIG. 21 in a partial sectional view, illustrates the end effector assembly of FIG. 1 where the deflection member is coupled to the hollow shaft.
Figure 22:
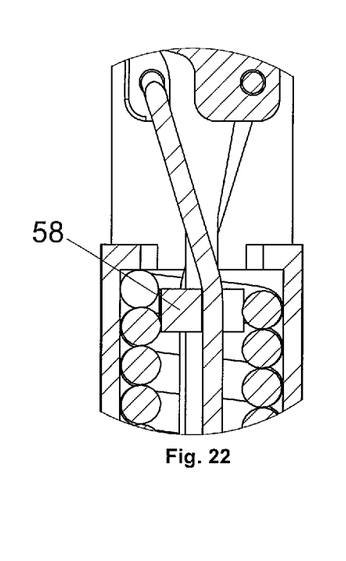
FIG. 22 in a partial sectional view, illustrates the end effector assembly of FIG. 21.
Figure 23:
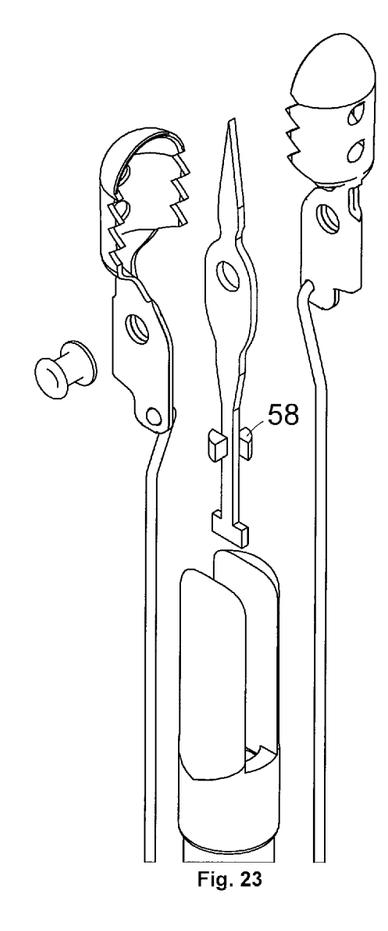
FIG. 23 in an exploded view, illustrates the end effector assembly of FIG. 21.
Figure 24:
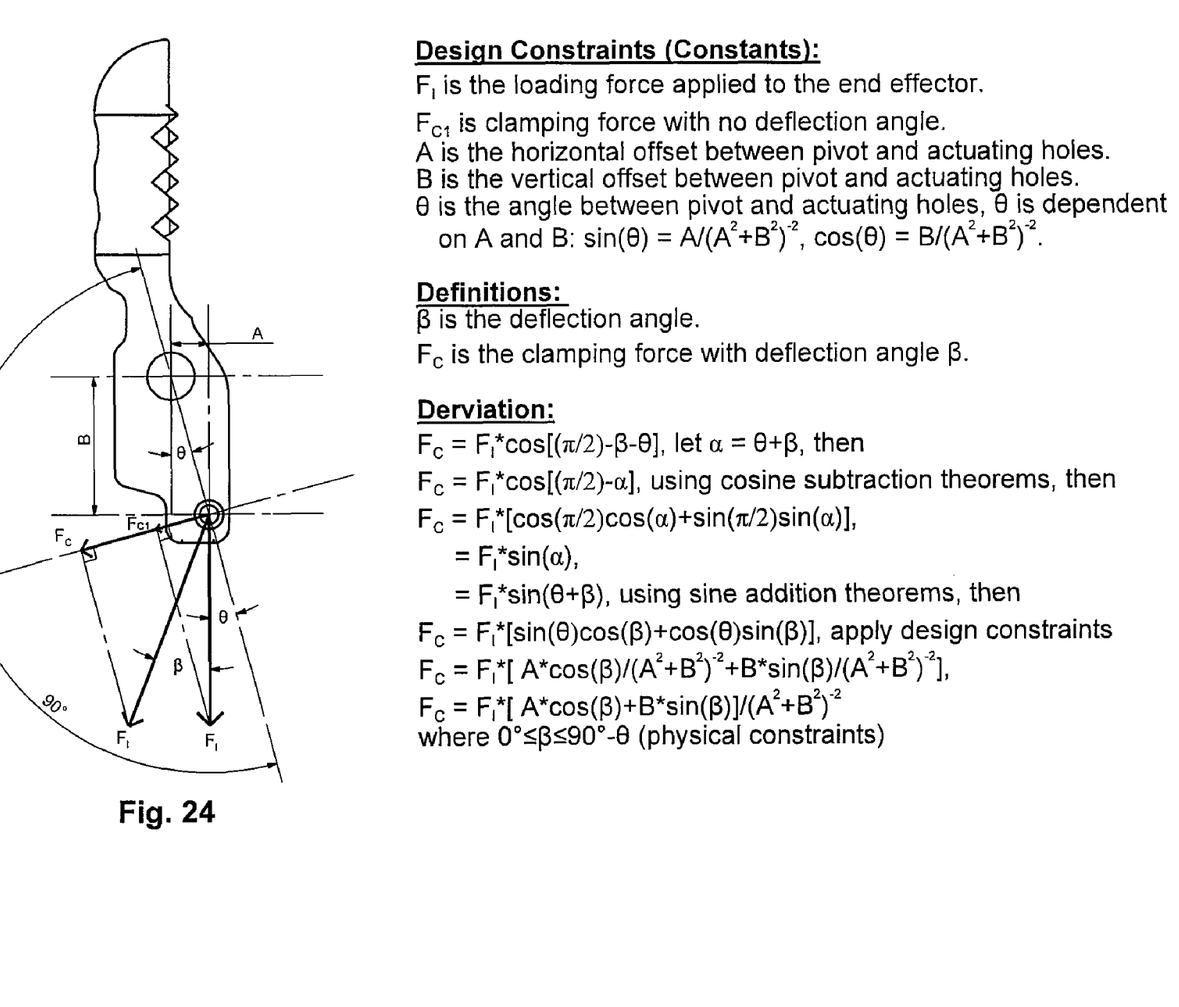
FIG. 24 in a schematic view with calculations, illustrates forces distribution in the end effector assembly when a deflection member is present.
Figure 25:
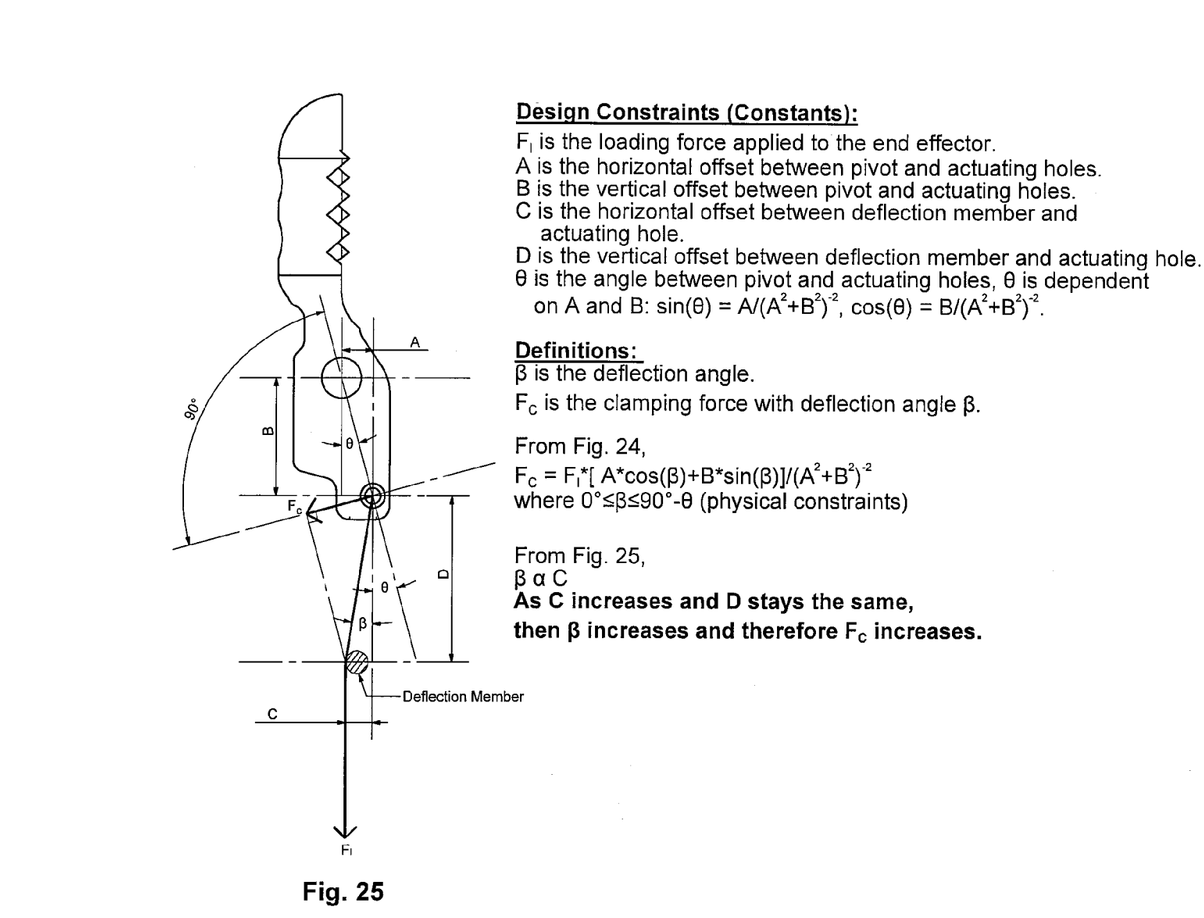
FIG. 25 in a schematic view, illustrates forces distribution in the end effector assembly when the deflection member is coupled to or integral with the hollow shaft.

Referring to FIGS. 21 to 23 in a fifth embodiment of the present invention, the deflection member 54 may be coupled to the hollow shaft 56. The deflection member 54 may be further defined as at least one shoulder 58 coupled to the hollow shaft 56. The shoulder 58 allows for the narrowing of the internal diameter of the hollow shaft 56. The decrease of the internal diameter by providing a surface for the actuation means 26 to engage with, allows for the deflection to occur and therefore results in the increased clamping force of the end effector assembly 10 when the procedural member assembly 24 is in the closed or nearly closed position. The shoulder 58 may further include a lubricious material for reducing friction when the actuation means 26 slide against the shoulder 58 to allow for smooth operation.

Figure 26:
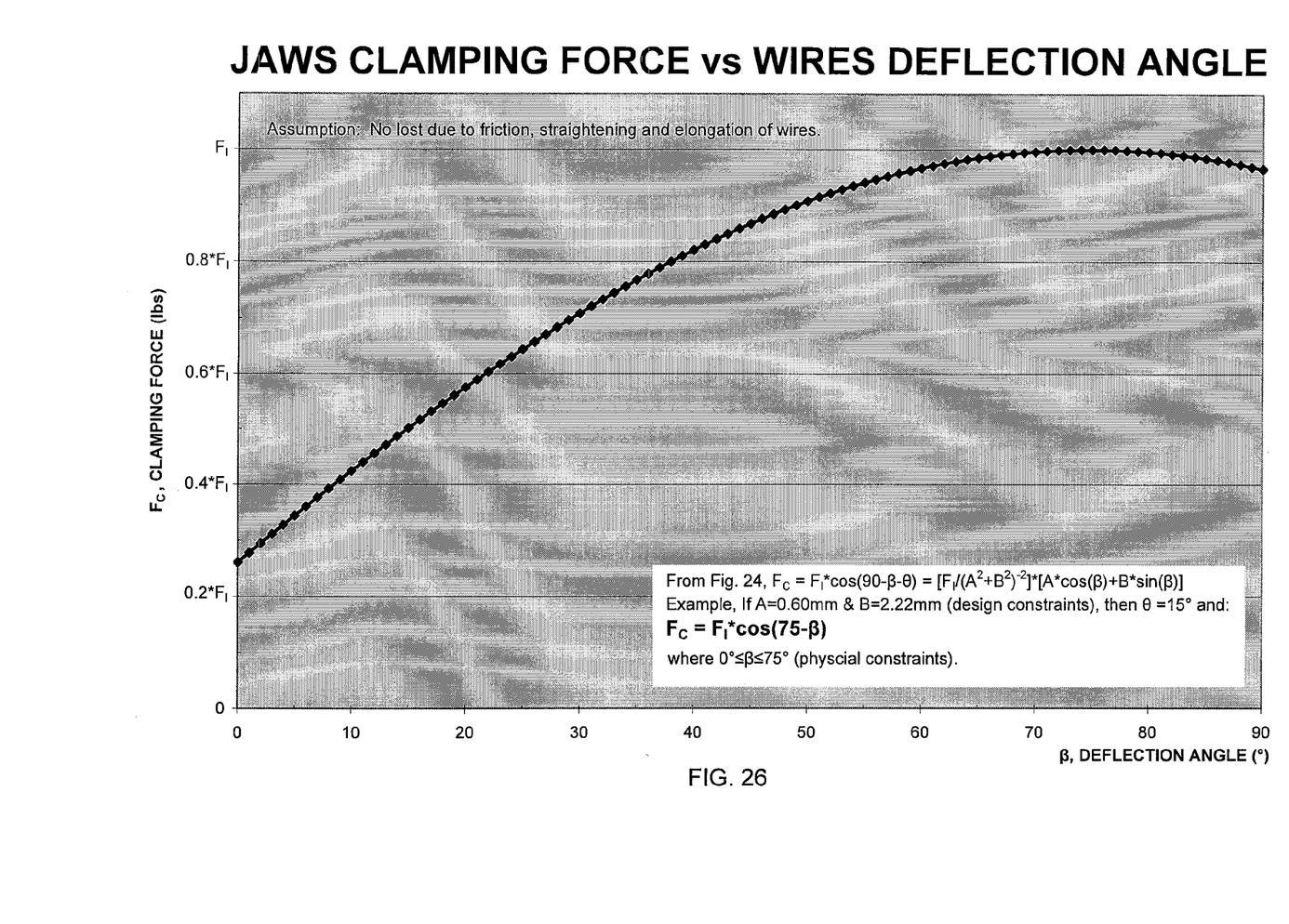
FIG. 26 in a schematic view, illustrates the increased clamping force $F_c$ with an increase in the deflection angle $\beta$ for given, as an example, design constrain A=0.60 mm and B=2.2 mm.

Referring to FIGS. 13 to 15 and FIGS. 24 to 26, all of the embodiments for the instant invention result in the engagement of the actuation means by the deflection members when the end effector assembly 10 is in operation. This results in an increased clamping force for the procedural member assembly when the procedural members are in the closed or nearly closed position. The positioning of the deflection members on the flat support can change the angle of deflection. As the deflection member is positioned closer to the distal end of the end effector assembly, the angle of deflection increases and the clamping force changes accordingly to the theoretic function $F_c(\beta) = F_1 * [A*\cos(\beta) + B*\sin(\beta)]/(A^2+B^2)^{-2}$. FIG. 26 illustrates the graph of the function for given design constrains A=0.60 mm and B=2.2 mm and not taking into consideration any loses due to friction, straightening, stretching or elongation of the actuation means. In this example the maximum clamping force occurs when the deflection angle $\beta_{max} = 75°$.

The end effector assembly may be used through an endoscope which can be rigid, semi rigid or flexible and is typically for a biopsy forceps. However the instant invention is not limited to biopsy forceps and can be applied to other endoscopic tools that can benefit from an increased clamping force, such as, surgical clip appliers, scissors, grabbers, retrievers, suturing devices, punches and combination of these devices.

It must be noted that, as used in the specification and the appended claims, the singular forms "a", "an" and "the" include plural references unless context clearly dictates otherwise.

Other variations and modifications of the invention are possible. All such modifications or variations are believed to be within the sphere and scope of the invention as defined by the claims appended hereto.

I claim:

1. An end effector assembly with increased clamping force for a surgical instrument comprising:
    (a) a hollow shaft having a proximal end and a distal end;
    (b) a clevis coupled to the distal end of the hollow shaft;
    (c) at least one deflection member integral with the clevis;
    (d) a procedural member assembly rotatably coupled to the clevis;
    (e) at least one actuation means attached to the procedural member assembly at an actuating hole and slidable relative to the hollow shaft for rotationally moving the procedural member assembly about a pivot point between a closed and an open position wherein the at least one deflection member integral with the clevis deflects inwards at least one actuation means changing the distribution of the loading force in the end effector assembly resulting in increased clamping force; the clamping force being defined as a force acting on the procedural member assembly at the actuating hole and perpendicular to a line defined by the centers of actuation and pivoting of the procedural member assembly, the value of the clamping force described by function:

$F_c(\beta)=F_1*[A*\cos(\beta)+B*\sin(\beta)]/(A^2+B^2)^{-2}$ wherein A is the horizontal offset between the pivot point and the actuating hole, B is the vertical offset between the pivot point and the actuating hole, $F_1$ is the loading force applied to the end effector, this function reaching its maximum value for $\beta_{max}$ with given design constraints, where $\beta$ is the deflection angle, and not considering any friction losses due to engagement of the surgical instrument.

2. An end effector assembly with increased clamping force for a surgical instrument as claimed in claim 1 wherein the deflection member is an integral shoulder for engaging at least one actuation means.

3. An end effector assembly with increased clamping force for a surgical instrument as claimed in claim 2 wherein the integral shoulder further comprises a lubricious material for reducing friction.

4. An end effector assembly with increased clamping force for a surgical instrument comprising:
   (a) a hollow shaft having a proximal end and a distal end;
   (b) a clevis coupled to the distal end of the hollow shaft;
   (c) a flat support coupled to the clevis;
   (d) at least one deflection member coupled to the clevis and the flat support;
   (e) a procedural member assembly rotatably coupled to the flat support;
   (f) at least one actuation means attached to the procedural member assembly at an actuating hole and slidable relative to the hollow shaft for rotationally moving the procedural member assembly about a pivot point between a closed and an open position wherein the at least one deflection member integral with the clevis deflects inwards at least one actuation means changing the distribution of the loading force in the end effector assembly resulting in increased clamping force; the clamping force being defined as a force acting on the procedural member assembly at the actuating hole and perpendicular to a line defined by the centers of actuation and pivoting of the procedural member assembly, the value of the clamping force described by function:

$F_c(\beta)=F_1*[A*\cos(\beta)+B*\sin(\beta)]/(A^2+B^2)^{-2}$ wherein A is the horizontal offset between the pivot point and the actuating hole, B is the vertical offset between the pivot point and the actuating hole, $F_1$ is the loading force applied to the end effector, this function reaching its maximum value for $\beta_{max}$ with given design constraints, where $\beta$ is the deflection angle, and not considering any friction losses due to engagement of the surgical instrument.

5. An end effector assembly with increased clamping force for a surgical instrument as claimed in claim 4 wherein the deflection member is at least one pin coupled to the clevis and the flat support through a series of apertures in the clevis and the flat support.

6. An end effector assembly with increased clamping force for a surgical instrument as claimed in claim 5 wherein the deflection member further comprises a lubricious material for reducing friction.

7. An end effector assembly with increased clamping force for a surgical instrument as claimed in claim 5 wherein the deflection member is rotatable within the apertures.

8. An end effector assembly with increased clamping force for a surgical instrument comprising:
   (a) a hollow shaft having a proximal end and a distal end;
   (b) a flat support;
   (c) at least one deflection member coupled to the flat support;
   (d) a procedural member assembly rotatably coupled to the flat support;
   (e) at least one actuation means attached to the procedural member assembly at an actuating hole and slidable relative to the hollow shaft for rotationally moving the procedural member assembly about a pivot point between a closed and an open position wherein the at least one deflection member integral with the clevis deflects inwards at least one actuation means changing the distribution of the loading force in the end effector assembly resulting in increased clamping force; the clamping force being defined as a force acting on the procedural member assembly at the actuating hole and perpendicular to a line defined by the centers of actuation and pivoting of the procedural member assembly, the value of the clamping force described by function:

$F_c(\beta)=F_1*[A*\cos(\beta)+B*\sin(\beta)]/(A^2+B^2)^{-2}$ wherein A is the horizontal offset between the pivot point and the actuating hole, B is the vertical offset between the pivot saint and the actuating hole, $F_1$ is the loading force applied to the end effector, this function reaching its maximum value for $\beta_{max}$ with given design constraints, where $\beta$ is the deflection angle, and not considering any friction losses due to engagement of the surgical instrument.

9. An end effector assembly with increased clamping force for a surgical instrument as claimed in claim 8 wherein the deflection member is at least one pin coupled to the flat support.

10. An end effector assembly with increased clamping force for a surgical instrument as claimed in claim 9 wherein the deflection member further comprises a lubricious material for reducing friction.

11. An end effector assembly with increased clamping force for a surgical instrument as claimed in claim 9 wherein the deflection member is rotatable within the aperture of the flat support.

12. An end effector assembly with increased clamping force for a surgical instrument comprising:
   (a) a hollow shaft having a proximal end and a distal end;
   (b) a flat support having a slot;
   (c) at least one deflection member moveably coupled within the slot of the flat support;
   (d) a procedural member assembly rotatably coupled to the flat support;
   (e) at least one actuation means attached to the procedural member assembly at an actuating hole and slidable relative to the hollow shaft for rotationally moving the procedural member assembly about a pivot point between a closed and an open position wherein the at least one deflection member integral with the clevis deflects inwards at least one actuation means changing the distribution of the loading force in the end effector assembly resulting in increased clamping force; the clamping force being defined as a force acting on the procedural member assembly at the actuating hole and perpendicular to a line defined by the centers of actuation and pivoting of the procedural member assembly, the value of the clamping force described by function:

$F_c(\beta)=F_1*[A*\cos(\beta)+B*\sin(\beta)]/(A^2+B^2)^{-2}$ wherein A is the horizontal offset between the pivot point and the actuating hole, B is the vertical offset between the pivot point and the actuating hole, $F_1$ is the loading force applied to the end effector, this function reaching its maximum value for $\beta_{max}$ with given design constraints, where $\beta$ is the deflection angle, and not considering any friction losses due to engagement of the surgical instrument.

13. An end effector assembly with increased clamping force for a surgical instrument as claimed in claim 12 wherein the deflection member is at least one pin movably coupled to slot in the flat support.

14. An end effector assembly with increased clamping force for a surgical instrument as claimed in claim 13 wherein the deflection member further comprises a lubricious material for reducing friction.

15. An end effector assembly with increased clamping force for a surgical instrument as claimed in claim 12 wherein the deflection member is rotatable within the slot of the flat member.

16. An end effector assembly with increased clamping force for a surgical instrument comprising:
   (a) a hollow shaft having a proximal end and a distal end;
   (b) at least one deflection member coupled to the hollow shaft;
   (c) a rotatable procedural member assembly;
   (d) at least one actuation means attached to the procedural member assembly at an actuating hole and slidable relative to the hollow shaft for rotationally moving the procedural member assembly about a pivot point between a closed and an open position wherein the at least one deflection member integral with the clevis deflects inwards at least one actuation means changing the distribution of the loading force in the end effector assembly resulting in increased clamping force; the clamping force being defined as a force acting on the procedural member assembly at the actuating hole and perpendicular to a line defined by the centers of actuation and pivoting of the procedural member assembly, the value of the clamping force described by function:
   $F_c(\beta)=F_1*[A*\cos(\beta)+B*\sin(\beta)]/(A^2+B^2)^{-2}$ wherein A is the horizontal offset between the pivot point and the actuating hole, B is the vertical offset between the pivot point and the actuating hole, $F_1$ is the loading force applied to the end effector, this function reaching its maximum value for $\beta_{max}$ with given design constraints, where $\beta$ is the deflection angle, and not considering any friction losses due to engagement of the surgical instrument.

17. An end effector assembly with increased clamping force for a surgical instrument as claimed in claim 16 wherein the deflection member is at least one shoulder coupled to the hollow shaft or at least one shoulder being an integral part of the hollow shaft.

18. An end effector assembly with increased clamping force for a surgical instrument as claimed in claim 17 wherein the deflection member further comprises a lubricious material for reducing friction.

19. An end effector assembly with increased clamping force for a surgical instrument as claimed in claim 1, 4, 8, 12 or 16 wherein the actuation means compromises of at least one filament.

20. An end effector assembly with increased clamping force for a surgical instrument as claimed in claim 1, 4, 8, 12 or 16 wherein design constrains A and B can be dynamically changed and dynamically change the clamping force $F_c$.

21. An end effector assembly with increased clamping force for a surgical instrument as claimed in claim 1, 4, 8, 12 or 16 wherein the position of the deflection member can vary changing the deflection angle $\beta$ and the value of the function $F_c(\beta)$.

* * * * *